(12) United States Patent
Biedermann et al.

(10) Patent No.: US 9,017,390 B2
(45) Date of Patent: Apr. 28, 2015

(54) POLYAXIAL BONE ANCHORING DEVICE

(71) Applicant: Biedermann Technologies GmbH & Co. KG, Donaueschingen (DE)

(72) Inventors: Lutz Biedermann, VS-Villingen (DE); Wilfried Matthis, Weisweil (DE); Bernd Fischer, Bräunlingen (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 172 days.

(21) Appl. No.: 13/673,837

(22) Filed: Nov. 9, 2012

(65) Prior Publication Data

US 2013/0123861 A1    May 16, 2013

Related U.S. Application Data

(60) Provisional application No. 61/559,326, filed on Nov. 14, 2011.

(30) Foreign Application Priority Data

Nov. 14, 2011 (EP) .................................... 11189042

(51) Int. Cl.
    *A61B 17/04*   (2006.01)
    *A61B 17/86*   (2006.01)
    *A61F 2/08*    (2006.01)
    *A61B 17/70*   (2006.01)

(52) U.S. Cl.
    CPC .......... *A61B 17/8605* (2013.01); *A61B 17/866* (2013.01); *A61B 17/7037* (2013.01)

(58) Field of Classification Search
    USPC .................................................. 606/300–321
    See application file for complete search history.

(56) References Cited

U.S. PATENT DOCUMENTS

| | | |
|---|---|---|
| 2007/0055242 A1 | 3/2007 | Bailly |
| 2007/0123862 A1 | 5/2007 | Warnick |
| 2009/0149887 A1 | 6/2009 | Schlaepfer et al. |
| 2011/0160779 A1* | 6/2011 | Schlaepfer et al. ........... 606/305 |
| 2011/0213419 A1 | 9/2011 | Richelsoph |

OTHER PUBLICATIONS

Extended European Search Report for European Application No. 11189042.2, European Search report dated Apr. 26, 2012 and mailed May 8, 2015 (5 pgs).

* cited by examiner

*Primary Examiner* — Sameh Boles
(74) *Attorney, Agent, or Firm* — Christie, Parker & Hale, LLP (57) ABSTRACT

A polyaxial bone anchoring device includes a bone anchoring element having a shank and a head, a head receiving part having a first end, an open second end, and a hollow interior portion for receiving the head therein, a locking ring configured to be mounted around the head receiving part and having a rod receiving portion, a cap configured to be connected to the head receiving part, the cap having a central axis and two opposite legs extending in a direction of the central axis, and a locking element configured to extend from the cap to lock relative positions of the bone anchoring element and an inserted rod relative to the head receiving part, wherein the cap is rotatable relative to the head receiving part between a first position in which the cap is movable and a second position in which the legs engage the head receiving part.

17 Claims, 12 Drawing Sheets

POLYAXIAL BONE ANCHORING DEVICE

CROSS-REFERENCE TO RELATED APPLICATION(S)

The present application claims the benefit of U.S. Provisional Patent Application Ser. No. 61/559,326, filed Nov. 14, 2011, the contents of which are hereby incorporated by reference in their entirety, and claims priority to European Patent Application EP 11 189 042.2, filed Nov. 14, 2011 the contents of which are hereby incorporated by reference in their entirety.

BACKGROUND

1. Field of the Invention

The invention relates to a polyaxial bone anchoring device including a bone anchoring element for anchoring in a bone or a vertebra, a head receiving part for receiving a head of the bone anchoring element, a locking ring mounted around the head receiving part for coupling a stabilization rod to the head receiving part and to the bone anchoring element, and a cap with a locking element for securing the rod and for locking the assembly. When the rod is mounted in a rod receiving portion of the locking ring and the cap is placed onto the assembly, the cap is rotatable with respect to the head receiving part between a first position in which the cap is out of engagement with the head receiving part and a second position in which the cap engages the head receiving part. The locking element exerts pressure onto the rod to move the locking ring to a position where the locking ring locks the head in the head receiving part. Simultaneously, the rod can be fixed by the locking element.

2. Description of Related Art

US 2009/0149887 A1 describes an apparatus for connecting a bone anchor to a support rod including a connector body, a sleeve around the connector body and a cap.

US 2011/0213419 A1 describes a screw and rod fixation assembly including a body member including a screw seat for seating a screw head therein and a rod seat for seating a rod therein. An adjustable locking ring applies a locking force against the screw head seated in the screw seat and a locking cap adjustably applies a locking force against a rod seated in the rod seat. The adjustable screw locking ring and locking cap function independent of each other.

SUMMARY

It is an object of embodiments of the invention to provide a polyaxial bone anchoring device having a wider range of applications, in particular, being more suitable for applications that require bone anchors with relatively small size.

The polyaxial bone anchoring device makes use of a cap and a locking element received in the cap for securing and fixing a rod and a head of a bone anchoring element. Therefore, a problem of splaying of portions of a receiving part when tightening the locking element, as known from conventional bone anchors, does not occur. Furthermore, with the cap, the bone anchoring device can have a lower profile in an axial or height direction of the bone anchoring device. This allows the bone anchoring device to be particularly suitable for use in the cervical spine or in pediatric applications where smaller bone anchoring devices are desired, trauma, and minimally invasive applications, or for using in other types of bone surgery.

With the polyaxial bone anchoring device according to embodiments of the invention, a modular bone anchoring system can be provided. The modular system can include a head receiving part preassembled with a locking ring, the cap preassembled with the locking element, and a set of various bone anchoring elements having different shanks. Various shanks with different diameter, thread form, or other different features can be combined with the head receiving part and locking ring according to the requirements of each particular clinical situation. Therefore, a surgeon or other practitioner has a more substantial or wider choice of implants. By such modularity, costs of stock-holding can also be decreased.

BRIEF DESCRIPTION OF THE DRAWINGS

Further features and advantages will become apparent from the description of embodiments by means of the accompanying drawings. In the drawings:

FIG. 15 shows a top view of the locking ring according to the first embodiment;

FIG. 16a shows a cross-sectional view of an assembled polyaxial bone anchoring device according to the first embodiment, the section being taken in a plane perpendicular to the rod axis;

FIG. 16b shows an enlarged view of a portion of FIG. 16a;

FIG. 36b shows an enlarged view of a portion of FIG. 36a;

DETAILED DESCRIPTION

Figure 1:
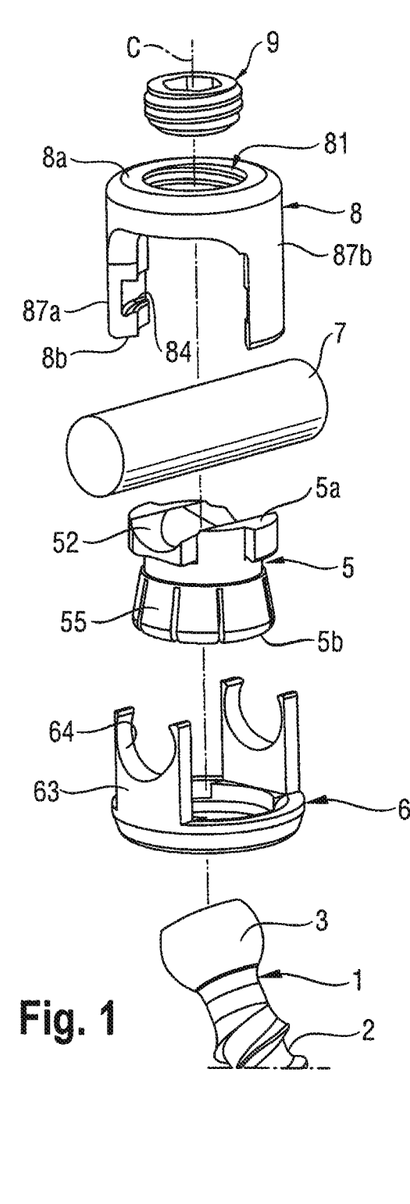
FIG. 1 shown an exploded perspective view of a polyaxial bone anchoring device according to a first embodiment.
Figure 2:
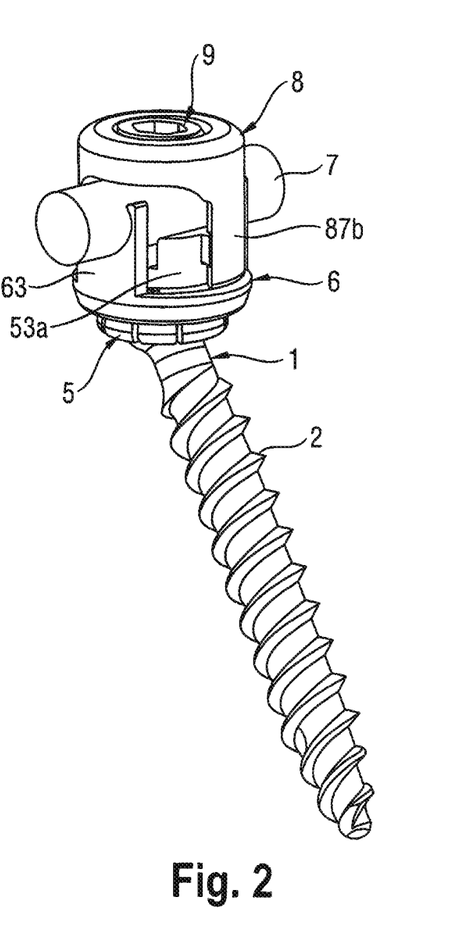
FIG. 2 shows a perspective view of the polyaxial bone anchoring device of FIG. 1 in an assembled state.
Figure 3:
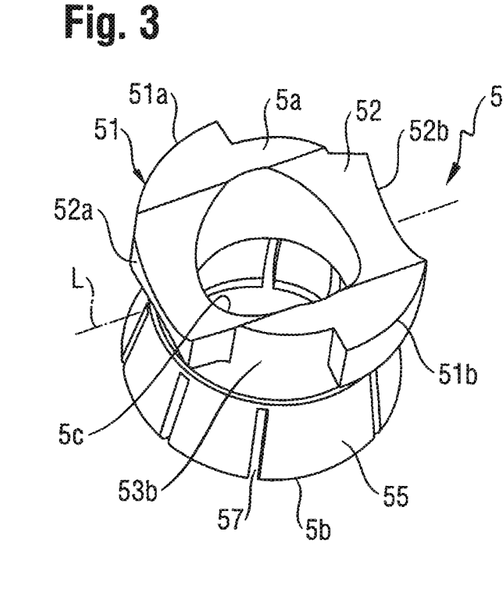
FIG. 3 shows a perspective view from a top of a head receiving part of the polyaxial bone anchoring device according to the first embodiment.
Figure 4:
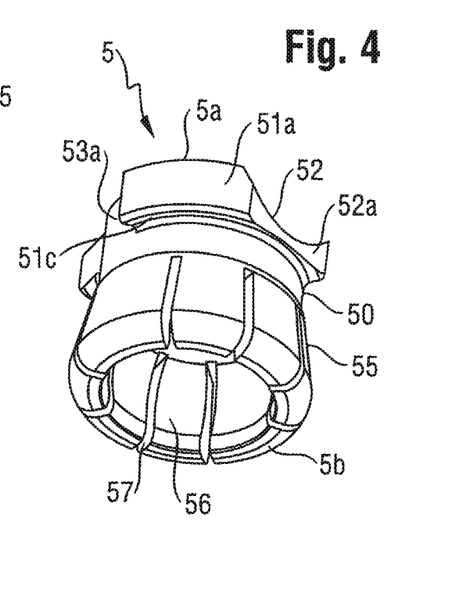
FIG. 4 shows a perspective view from a bottom of the head receiving part according to the first embodiment.
Figure 5:
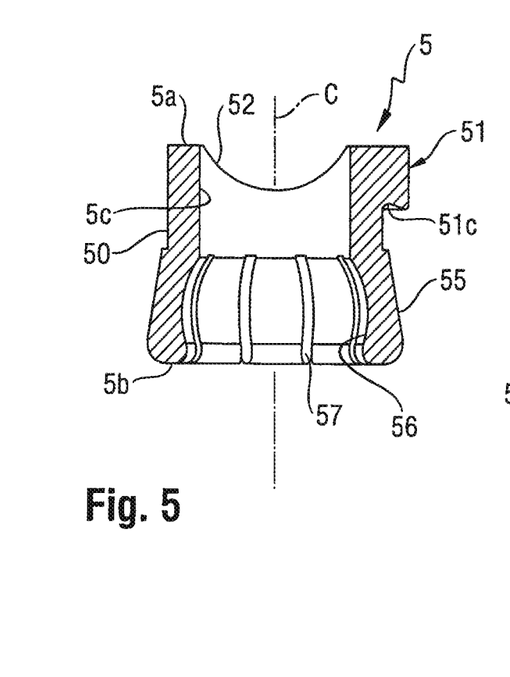
FIG. 5 shows a cross-sectional view of the head receiving part according to the first embodiment, where the section has been taken perpendicular to an axis of an inserted rod and slightly offset from a center of the head receiving part.
Figure 6:
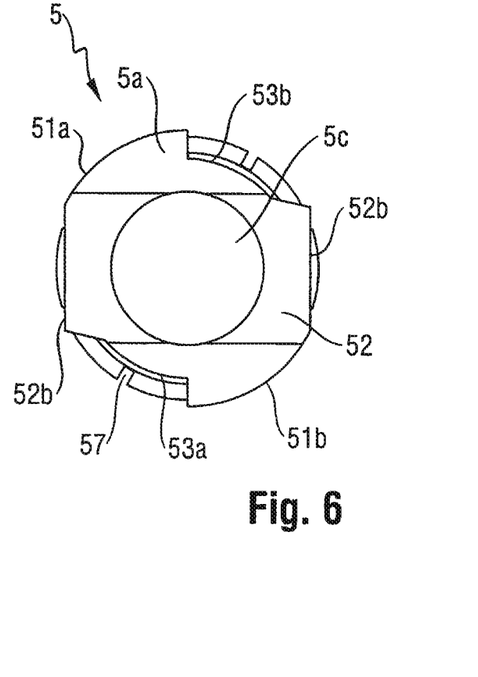
FIG. 6 shows a top view of the head receiving part according to the first embodiment.
Figure 7:
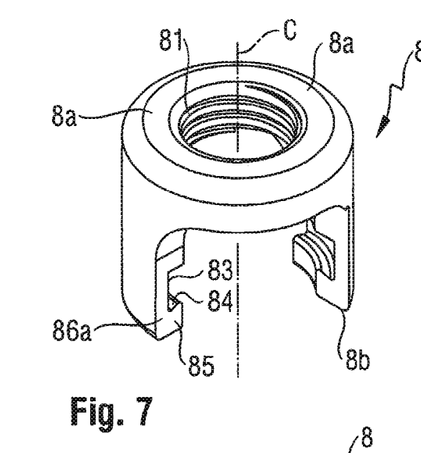
FIG. 7 shows a perspective view from a top of a cap of the polyaxial bone anchoring device according to the first embodiment.
Figure 8:
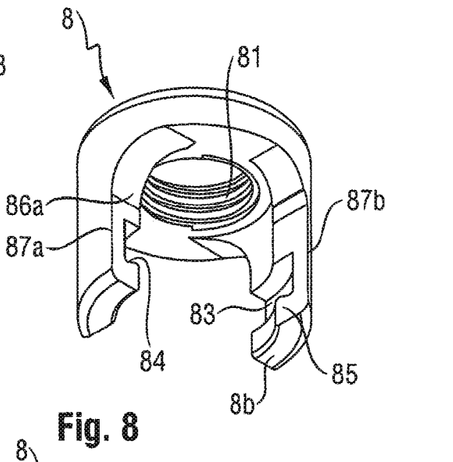
FIG. 8 shows a perspective view from a bottom of the cap according to the first embodiment.
Figures 9, 10:
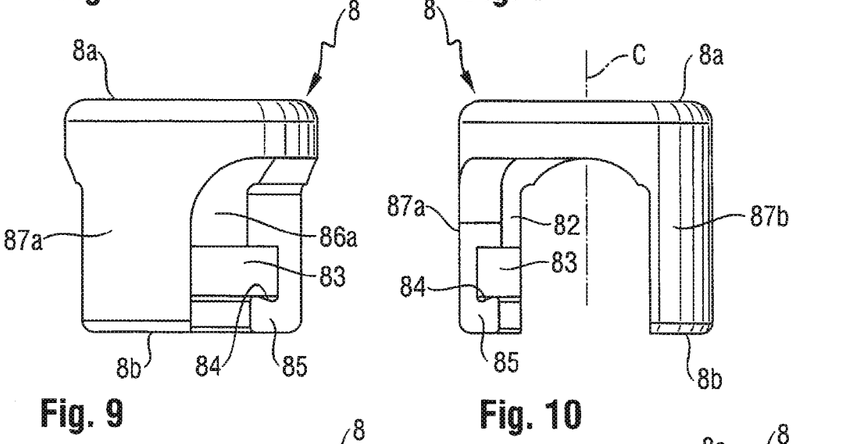
FIG. 9 shows a side view of the cap according to the first embodiment.
FIG. 10 shows another side view of the cap, rotated by 90° from FIG. 9, according to the first embodiment.
Figure 11:
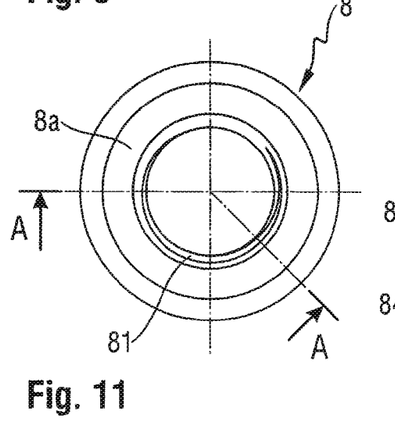
FIG. 11 shows a top view of the cap according to the first embodiment.
Figure 12:
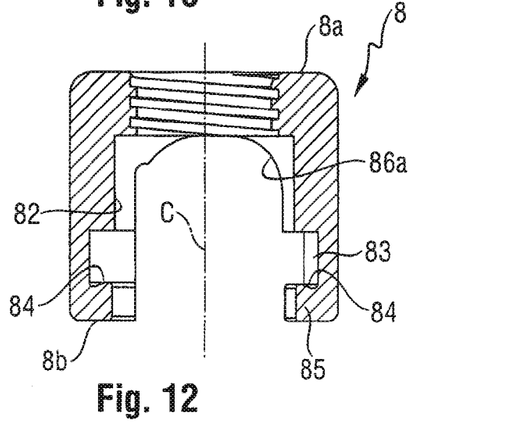
FIG. 12 shows a cross-sectional view of the cap according to the first embodiment, the cross-section taken along line A-A in FIG. 11.

As shown in FIGS. 1 and 2, a polyaxial bone anchoring device according to a first embodiment includes a bone anchoring element 1 in the form of a bone screw having a shank 2 with a threaded portion and a spherical segment-shaped head 3. The head 3 has a recess 4 (see FIG. 16a) for engagement with a tool. The bone anchoring device further includes a head receiving part 5 for receiving the head 3 of the bone anchoring element 1, and a locking ring 6 for receiving a rod 7, for example, a spinal stabilization rod, and for connecting the rod 7 to the bone anchoring element 1. In addition, the bone anchoring device includes a cap 8 for securing the rod 7 and a locking element 9 in the form of a set screw for locking the rod 7 and the head 3 relative to the rest of the bone anchoring device.

Referring in particular to FIGS. 3 to 6, the head receiving part 5 has a first end 5a and an opposite second end 5b, a central axis C and a coaxial through hole 5c. At the first end 5a, the head receiving part 5 has a cylindrical portion 50 with an outwardly extending flange or rim 51. A cylinder-segment-shaped recess 52 is formed at the first end 5a. The recess 52 serves as a seat for guiding the rod 7. At both ends of the cylinder-segment-shaped recess 52, the rim 51 is flattened, resulting in opposite flat surfaces 52a, 52b. At an angle to an axis L of the recess 52, there are cutouts 53a, 53b from the rim 51, so that two opposite rim portions 51a, 51b extend outward in a radial direction. The rim portions 51a, 51b extend in a circumferential direction substantially between the end of the rod guiding recess 52 up to an angle of around 90° relative to the axis L. A base surface of the cutouts 53a, 53b is cylindrical (e.g., forming part of cylindrical portion 50). The rim portions 51a, 51b each have on their side facing away from the first end 5a a circumferentially extending undercut portion 51c. The undercut portion 51c is formed by a surface that is inclined outwards and towards the second end 5b. The undercut portion 51c serves for engagement with a portion of the cap 8. The cylindrical portion 50 continues into a conically-shaped outer surface portion 55 widening towards the second end 5b. Further, an internal hollow spherical section 56 forming an accommodation space and a seat for spherical segment-shaped head 3 of the bone anchoring element 1 is formed in the head receiving part 5. The internal hollow spherical section 56 is configured to encompass the head 3 of the bone anchoring element 1 from the side, covering a region including a largest diameter of the head 3.

A plurality of slits 57 are provided that are open to the second end 5b. The slits 57 extend substantially through the wall of the internal hollow section 56 and render the head receiving part 5 flexible in a region where the head 3 is received. By the size and the number of the slits 57, a desired elasticity is provided to the head receiving part 5. The elasticity of the head receiving part 5 is such that the head 3 of the bone anchoring element 1 can be inserted by expanding the head receiving part 5, and can be clamped therein by compressing the head receiving part 5.

Referring to FIGS. 7 to 12, the cap 8 is a substantially cylindrical part with a first end 8a and an opposite second end 8b. At the first end 8a, there is a coaxial threaded through hole 81 for receiving the locking element 9. A coaxial bore 82 having a greater diameter than the threaded through hole 81 extends from the second end 8b to a distance from the first end 8a. The threaded through hole 81 opens into the coaxial bore 82. At a distance from the second end 8b, a circumferential groove 83 is provided that has a lower inclined wall. By means of this, the cap 8 has adjacent its second end 8b an inwardly directed rim 85 with the inclined wall forming an undercut portion 84. The incline of the undercut portion 84 corresponds substantially to the incline of the undercut portion 51c of the head receiving part 5.

The cap 8 further has two opposite substantially cuboid or rectangular shaped recesses 86a, 86b that extend from the second end 8b to a distance from the first end 8a. The recesses 86a, 86b may have rounded edges. By means of the recesses 86a, 86b, two opposite longitudinal legs 87a, 87b are formed in the lower portion of the cap 8. The recesses 86a, 86b have such a height and width that the cap 8 is configured to cover the rod 7 when the rod 7 is mounted to the head receiving part 5 and the locking ring 6. Further, the recesses 86a, 86b have a width in a circumferential direction that is substantially greater than a diameter of the rod 7, so that the legs 87a, 87b are configured to it into a space between the locking ring 6 and the rim portions 51a, 51b, at positions of the cutouts 53a, 53b. In other words, the legs 87a, 87b have a width in a circumferential direction that is smaller or equal to the width of the cutouts 53a, 53b of the head receiving part 5.

The locking element 9 in the form of a set screw is configured to be screwed into the threaded through hole 81. Although the thread of the cap 8 is shown to be a flat thread, any other thread form, such as a metric thread, can be used.

Referring to FIGS. 13 to 16b, the locking ring 6 has a ring portion 60 with a first end 6a and an opposite second end 6b. An outer surface of the ring portion 60 may be slightly conical, tapering towards the second 6b, to reduce a size of the bone anchoring device in a radial direction. The ring portion 60 has a curved internal surface portion 62, wherein the curvature is directed towards a center of the locking ring 6. The curved surface portion 62 can have a cross-section having a circular curvature, but other types of curvatures are also possible. An inner diameter of the locking ring 6 is such that the locking ring 6 can slide along the outer conical surface portion 55 of the head receiving part 5, thereby compressing the head receiving part 5 increasingly when sliding downwards (e.g., towards second end 5b).

Figure 13:
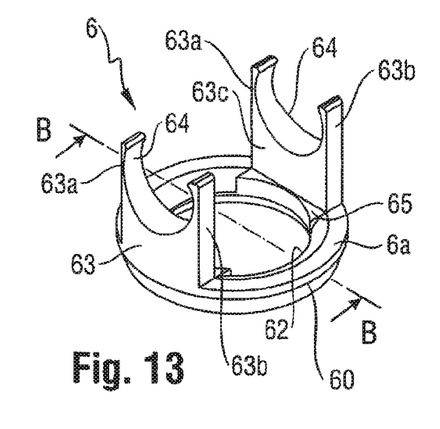
FIG. 13 shows a perspective view of a locking ring of the polyaxial bone anchoring device according to the first embodiment.
Figures 15, 16A, 16B:
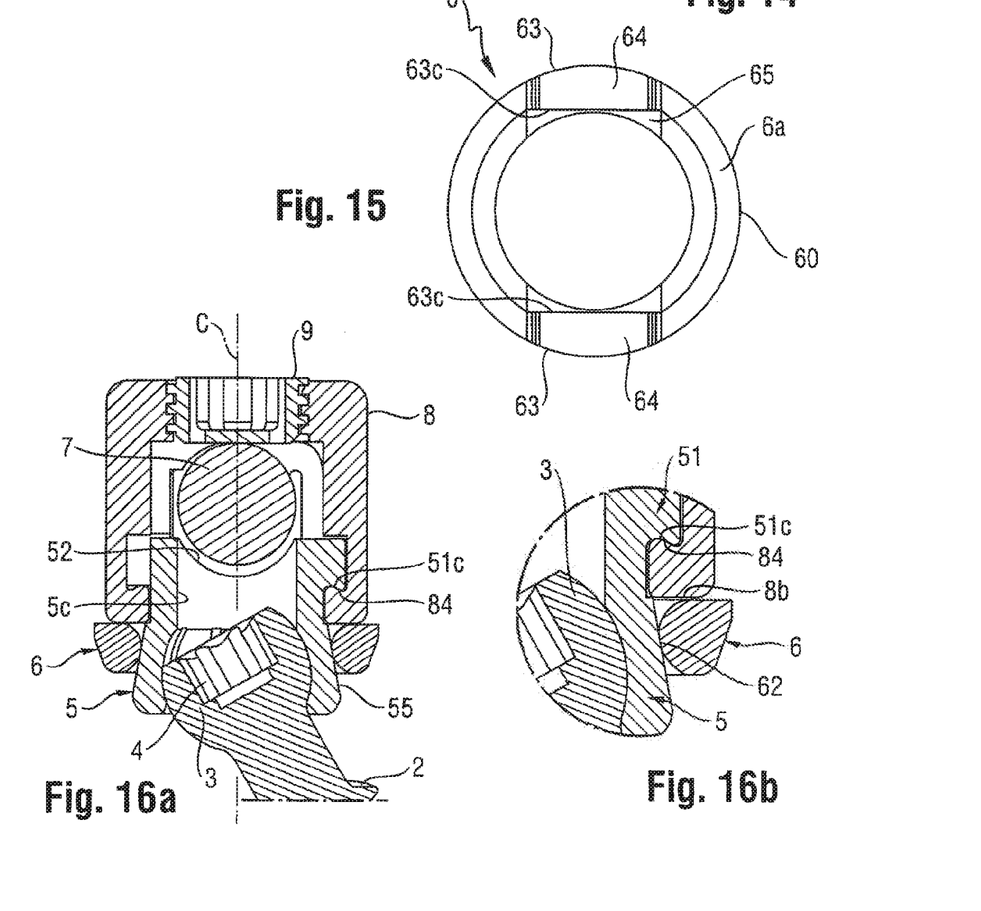

At the first end 6a, the locking ring 6 includes two projections 63 located diametrically opposite to each other. The projections 63 have a height such that they project up and away from the first end 5a of the head receiving part 5 when the locking ring 6 is mounted around the head receiving part 5, as depicted, for example, in FIG. 18. At their free ends, the projections 63 each have a recess 64 that has a shape of a segment of a circle including at least a portion with a greatest diameter of said circle. The diameter of the circular segment-shaped recess 64 corresponds substantially to the diameter of the rod 7. By means of the recess 64, each projection 63 has two upstanding legs 63a, 63b, that allow the rod 7 to be caught or held therein. As seen in FIGS. 13 and 15, a side 63c of the projections 63 that faces a central axis of the locking ring 6 may be flat.

Figure 14:
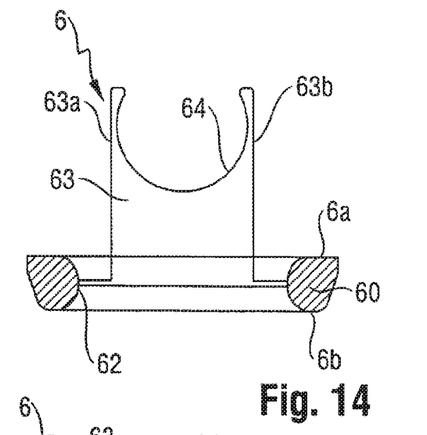
FIG. 14 shows a cross-sectional view of the locking ring according to the first embodiment, the cross-section taken along line B-B in FIG. 13.

The locking ring 6 may further include, at a position of the projections 63, on an, inside of the locking ring 6 at the first end 6a two inwardly projecting surfaces 65. The surfaces 65 may act as stops, for example, for cap 8 when the bone anchoring device is assembled.

The flexibility of the head receiving part 5 and a size of the head receiving part 5 at the open second end 5b allows mounting of the locking ring 6 from the second end 5b. When the locking ring 6 is mounted onto the head receiving part 5, the locking ring 6 is prevented from rotation around the head receiving part 5 due to the flat surfaces 52a, 52b of the head receiving part 5 facing and engaging the flat sides 63c of the projections 63. Dimensions of the respective parts can be designed such that the head 3 is preliminarily held in the head receiving part 5 by a slight friction force, and the locking ring 6 can also be held by a friction force in a preliminary manner around the head receiving part 5.

As can be seen in FIGS. 1, 3, and 16a to 16b the head receiving part 5, the locking ring 6, and the cap 8 are configured to allow a placement of the cap 8 onto or over the locking ring 6 with inserted rod 7 in a first position, in which the legs 87a, 87b extend into the cutouts 53a, 53b of the head receiving part 5. The cap 8 and the head receiving part 5 are further configured to allow a rotation of the cap 8 to a second position in which the undercut portion 84 of the cap 8 engages the undercut portion 51c of the head receiving part 5. In the second position, the cap 8 is prevented from being pulled off of the head receiving part 5 in a direction along the central axis C of the head receiving part 5.

The head receiving part 5, the locking ring 6, the cap 8, and the locking element 9, as well as the bone anchoring element 1, are made of bio-compatible materials, for example, of titanium or stainless steel, of bio-compatible alloys, such as nickel-titanium alloys, for example, Nitinol, or of a bio-compatible plastic material, such as, for example, polyetheretherketone (PEEK). The parts can be made of the same or of different materials.

Figure 17:
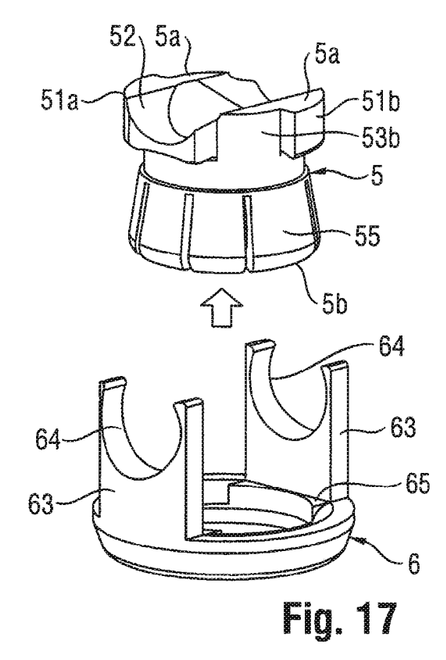
FIGS. 17 to 22 show steps of assembly and use of the polyaxial bone anchoring device according to the first embodiment.
Figure 18:
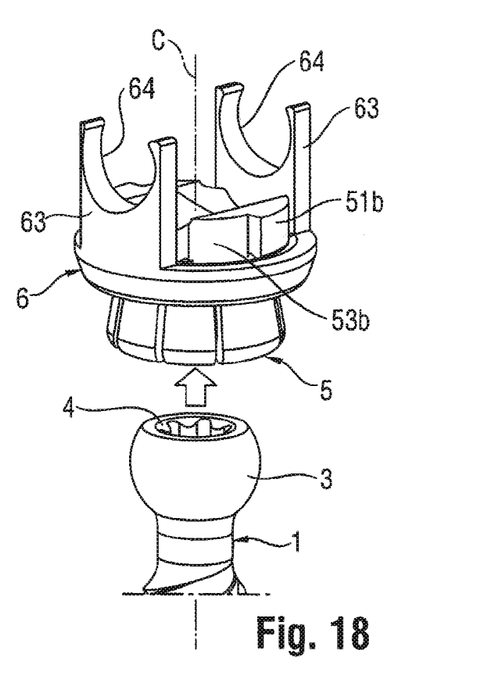

Referring to FIGS. 17 to 22, steps of mounting and use of the polyaxial bone anchoring device will be explained. As shown in FIG. 17, the locking ring 6 is mounted from the second end 5b to the head receiving part 5 such that, as shown in FIG. 18, the projections 63 for receiving the rod 7 extend upwards from the first end 5a of the head receiving part 5. An orientation of the locking ring 6 relative to the head receiving part 5 is such that the projections 63 are aligned with the cylinder-segment shaped recess 52 of the head receiving part 5. The rim portion 51 at the positions of the ends of the recess 52 may be supported by the support surfaces 65 of the locking ring 6. The head receiving part 5 and the locking ring 6 may be delivered in a pre-assembled manner.

In a second step, shown in FIG. 18, the bone anchoring element 1, with a suitable shank 2 for a specific clinical application, is mounted from the second end 5b to the assembly formed by the head receiving part 5 and the locking ring 6. The locking ring 6 may be in an uppermost position. The head 3 is introduced into the internal hollow section 56 of the head receiving part 5. This is facilitated by the head receiving part 5 being flexible.

At this stage, the modularity of the bone anchoring device allows combining of a bone anchoring element with a specific shank with the head receiving part 5 during or before surgery. The polyaxial bone anchoring device, thus assembled, is then inserted into a bone or a vertebra. In an alternative way of use, the bone anchoring element is first inserted into the bone or into the vertebra, and thereafter, the assembly including the head receiving part 5 and locking ring 6 is mounted to the head after implantation of the screw.

Figure 19:
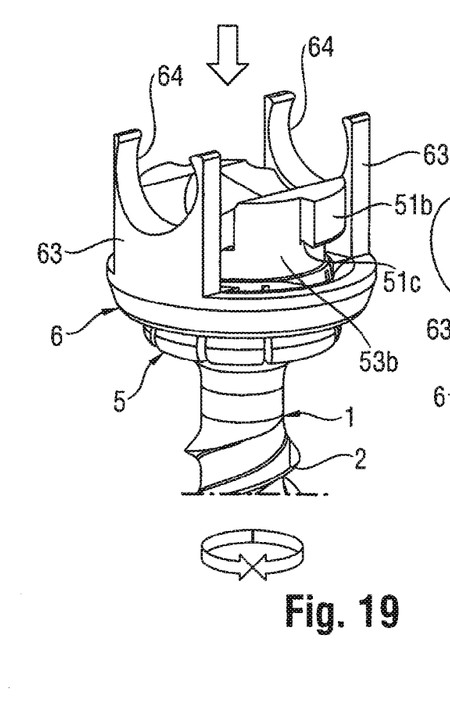

Then, as shown in FIG. 19, the locking ring 6 is shifted downwards, so that the locking ring 6 compresses the head receiving part 5. Here, the head 3 can be held in a preliminary angular position, and the locking ring 6 may also be held in this position, for example, by frictional forces acting between the head receiving part 5 and the head 3 on the one hand and between the locking ring 6 and the head receiving part 5 on the other hand.

Figure 20:
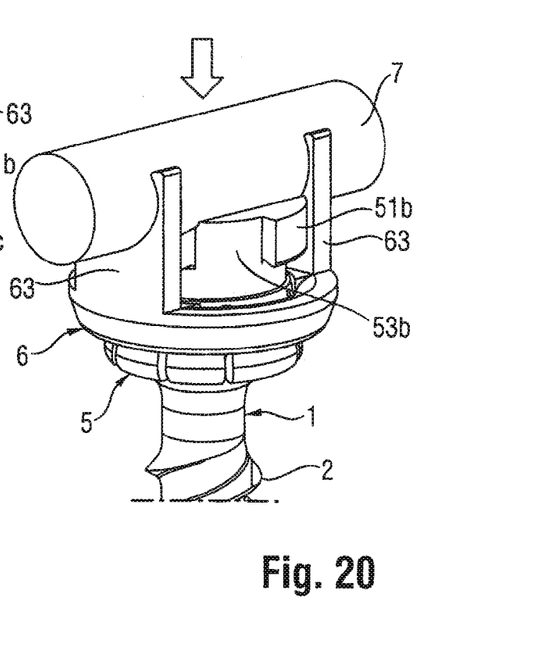

In a next step, as shown in FIG. 20, the rod 7 is inserted into the recesses 64 of the projections 63. Because the recesses 64 have circular segment shapes including more than a largest diameter of the circle, the rod 7 can be caught or held in the recesses 64, so that the rod 7 is preliminarily held in place therein.

Figure 21:
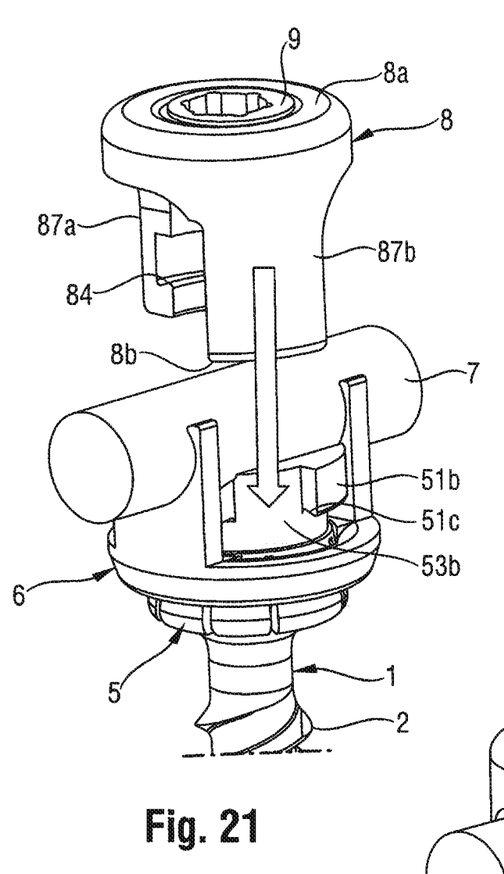
Figure 22:
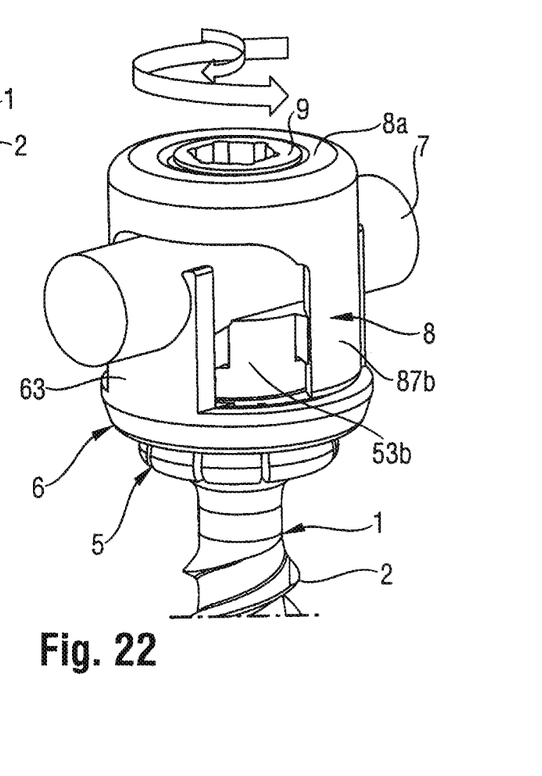
Figure 23:
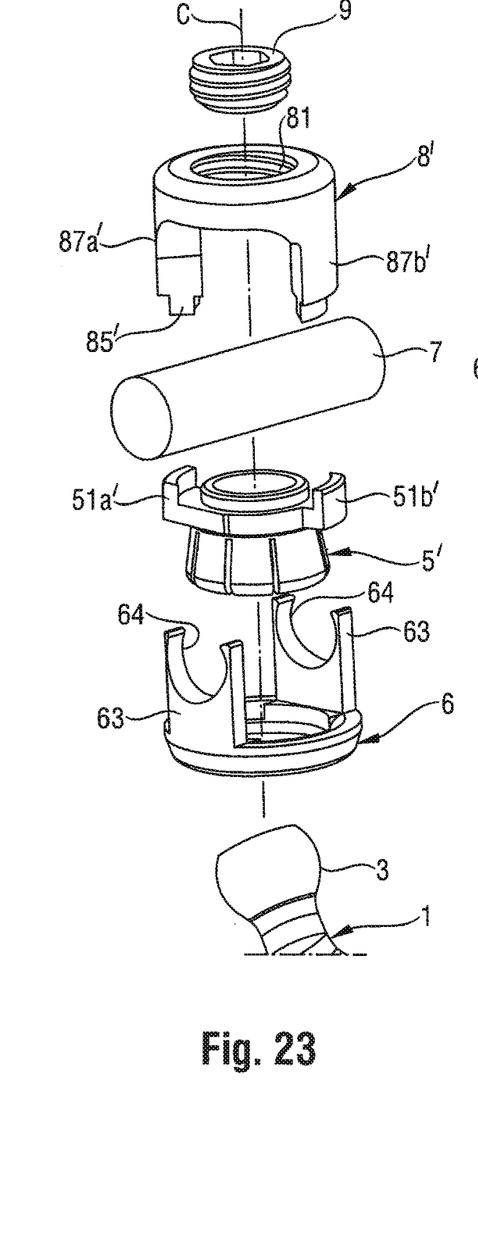
FIG. 23 shows an exploded perspective view of a polyaxial bone anchoring device according to a second embodiment.
Figure 24:
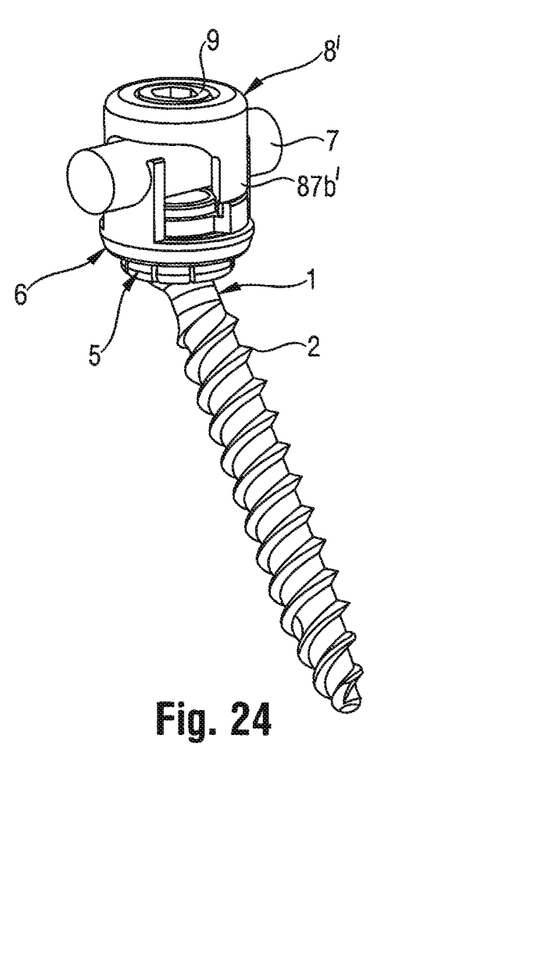
FIG. 24 shows a perspective view of the polyaxial bone anchoring device according to the second embodiment in an assembled state.
Figure 25:
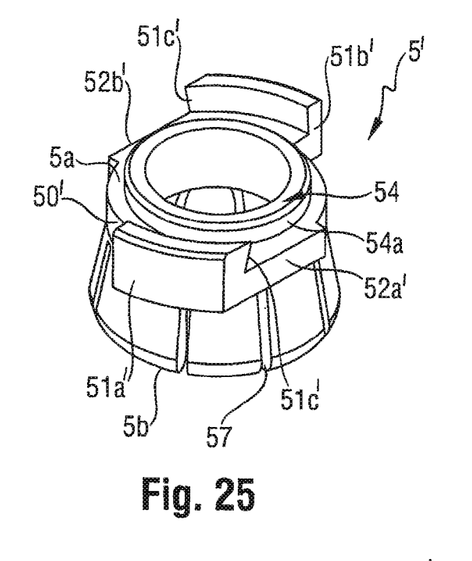
FIG. 25 shows a perspective view from a top of a head receiving part of the polyaxial bone anchoring device according to the second embodiment.
Figure 26:
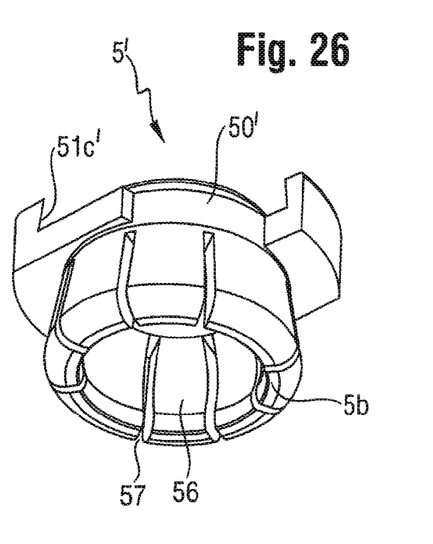
FIG. 26 shows a perspective view from a bottom of the head receiving part according to the second embodiment.
Figure 27:
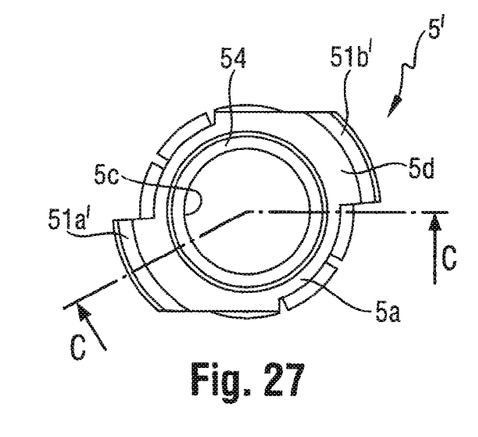
FIG. 27 shows a top view of the head receiving part according to the second embodiment.
Figure 28:
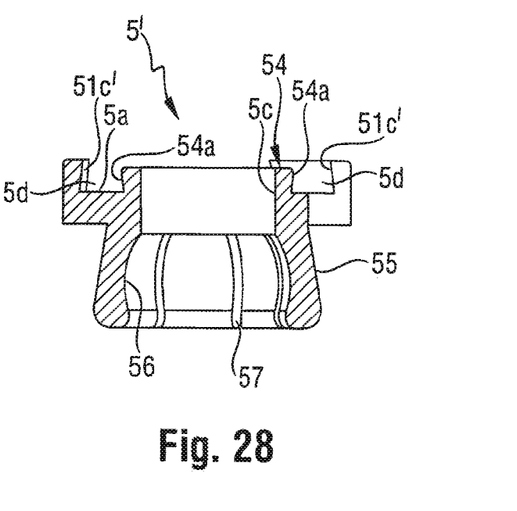
FIG. 28 shows a cross-sectional view of the head receiving part according to the second embodiment, the cross-section being taken along line C-C in FIG. 27.
Figures 29, 30:
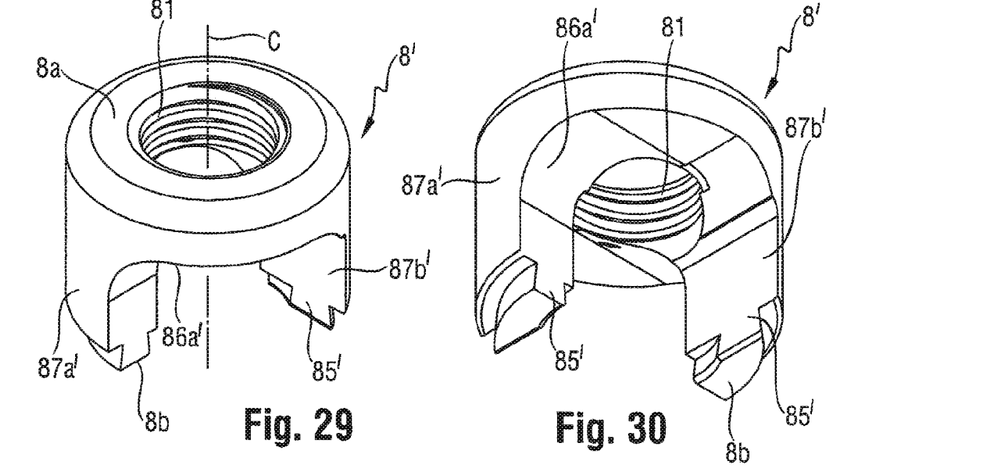
FIG. 29 shows a perspective view of a top of a cap of the polyaxial bone anchoring device according to the second embodiment.
FIG. 30 shows a perspective view from a bottom of the cap according to the second embodiment.
Figures 31, 32:
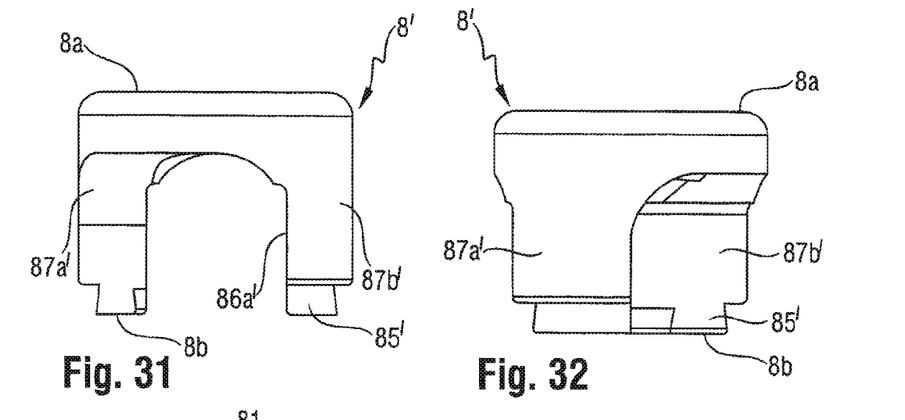
FIG. 31 shows a side view of the cap according to the second embodiment.
FIG. 32 shows a side view of the cap of the second embodiment, rotated by 90° from FIG. 31.
Figure 33:
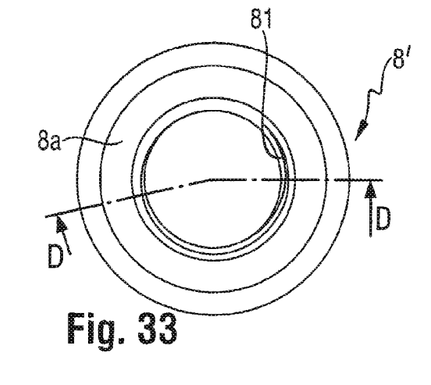
FIG. 33 shows a top view of the cap according to the second embodiment.
Figure 34:
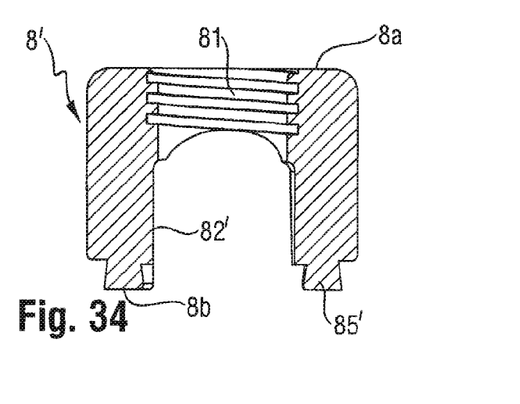
FIG. 34 shows a cross-sectional view of the cap according to the second embodiment, the cross-section being taken along line D-D in FIG. 33.

In a next step, as shown in FIG. 21, the cap 8 is placed onto the assembly. The locking element 9 may be pre-assembled with the cap 8. In a first position, the legs 87a, 87b extend along or are aligned with the cutouts 53a, 53b. By means of this, the legs 87a, 87b extend into the space between the projections 63 of the locking ring and the rim portions 51a, 51b of the head receiving part 5. Next, as shown in FIG. 22, the cap 8 is rotated so that the undercut portions 84 engage the undercut portions 51c at the rim portions 51a, 51b of the head receiving part 5. In this second position, the cap 8 is prevented from being pulled away from the head receiving part 5 in an axial direction. Then, the locking element 9 is tightened. The lower surface of the locking element 9 contacts the rod 7, and the rod 7 is pressed into the recesses 64 of the projections 63 of the locking ring 6. The force acting onto the rod 7 is thereby transferred to the locking ring 6, and the locking ring 6 is shifted downwards until it firmly compresses the head receiving part 5 and locks the head 3. Hence, the head 3 and the rod 7 are locked simultaneously relative to the rest of the bone anchoring device.

A second embodiment of a polyaxial bone anchoring device will be described with reference to FIGS. 23 to 36b. Parts and portions that are identical or similar to the parts and portions of the first embodiment are designated with the same reference numerals, and the descriptions thereof shall not be repeated. The bone anchoring device according to the second embodiment differs from the bone anchoring device according to the first embodiment in the design of the head receiving part and the cap.

As shown in particular in FIGS. 23 to 28, the head receiving part 5' does not include a rod guiding recess. Instead, the head receiving part 5' includes a first cylindrical portion 50' and an outwardly extending rim including two opposite radially and circumferentially extending brackets 51a', 51b', with upstanding rims having an undercut portion 51c'. Each bracket 51a', 51b' has a flattened side so that opposite flat surfaces 52a', 52b' are formed at an outer circumference of the cylindrical portion 50'. Between the flat surfaces 52a', 52b' and the brackets 51a', 51b', there may also be cylindrical surfaces. Furthermore, the head receiving part 5' includes at the first end 5a an upstanding circular rim 54 with a diameter smaller than an outer diameter of the cylindrical portion 50'. At an outside of the rim 54, there is an inclined surface 54a with an incline opposite to the incline of the undercut portion 51c' so that surface 54a forms together with the undercut portion 51c' a substantially dovetail-shaped groove 5d, as can be seen in particular in FIG. 28. Meanwhile, a portion of rim 54 not aligned with undercut portion 51c' may not have the inclined surface 54a, and may instead be cylindrical, for example, to allow the legs of the cap 8' to be inserted from above. The lower portion of the head receiving part 5' is identical or similar to that of the head receiving part 5 of the first embodiment.

Referring to FIGS. 29 to 34, the cap 8' according to the second embodiment differs from the cap 8 according to the first embodiment in that the cap 8' has a coaxial bore 82' that has a diameter only slightly larger than a diameter of the threaded through hole 81'. Cuboid or rectangular shaped recesses 86a', 86b' define longitudinally extending legs 87a', 87b' of the cap 8'. At a second end 8b, the cap 8' includes dovetail-shaped portions 85' that cooperate with the dovetail-shaped grooves 5d at the head receiving part 5'. The polyaxial bone anchoring device according to the second embodiment may have an even more reduced height than the first embodiment.

Figure 35:
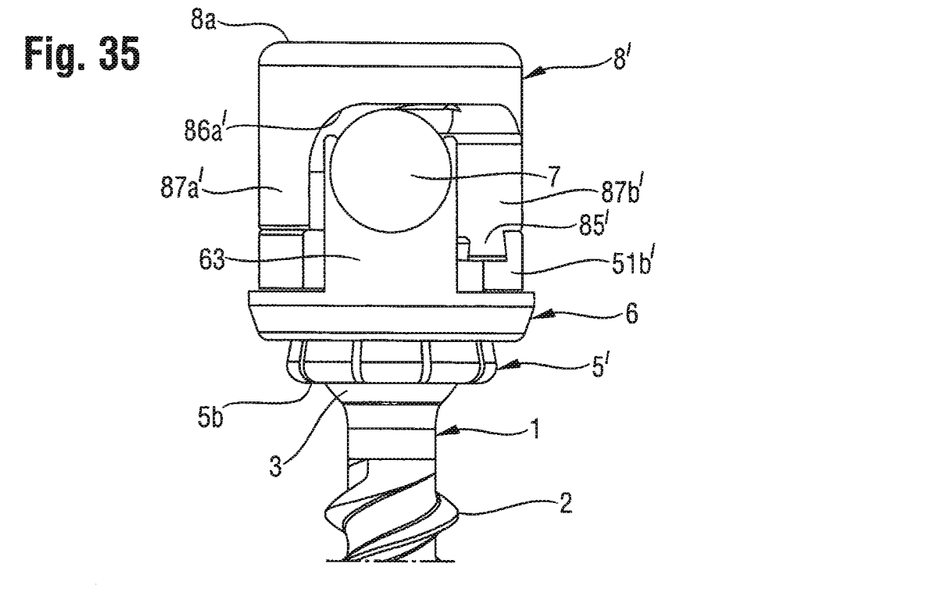
FIG. 35 shows a side view of the polyaxial bone anchoring device according to the second embodiment in an assembled state, seen in a direction along the rod axis.
Figure 36A:
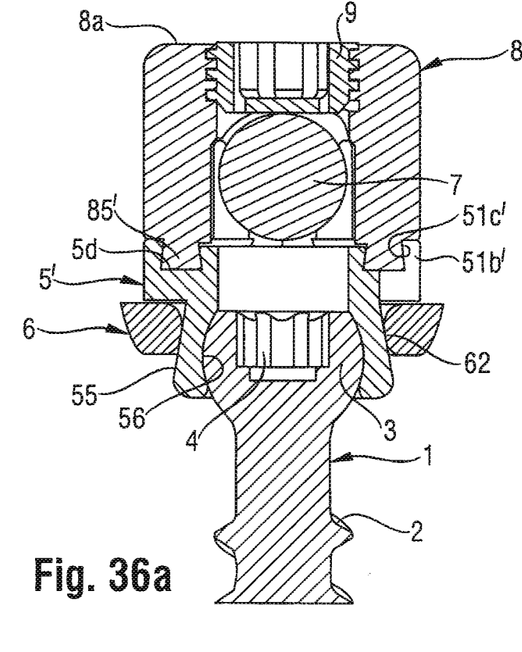
FIG. 36a shows a cross-sectional view of the polyaxial bone anchoring device according to the second embodiment shown in FIG. 35.
Figure 36B:
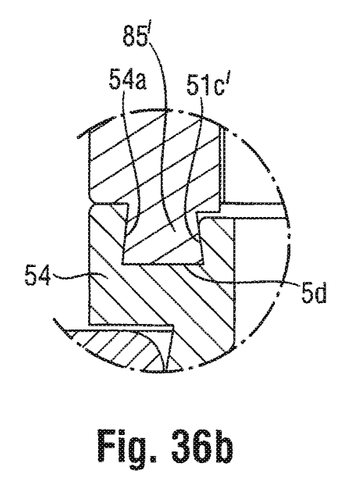

Hence, when the cap 8' is placed on the assembly including anchoring element 1, head receiving part 5', and locking ring 6, in a first position, the legs 87a', 87b' extend along cylindrical portions of the head receiving part. Then, as shown in FIGS. 35, 36a, and 36b, the cap 8' can be rotated, thereby engaging the dovetail-shaped rims 85' with the dovetail-shaped grooves 5d at the head receiving part 5', so that the cap 8' is connected to the head receiving part 5', and the rod 7 is secured against removal. The dovetail shapes prevent pulling off of the cap 8' in an axial direction relative to the head receiving part 5'. Then, the locking element 9 can be tightened to fix the whole assembly.

Figure 37A:
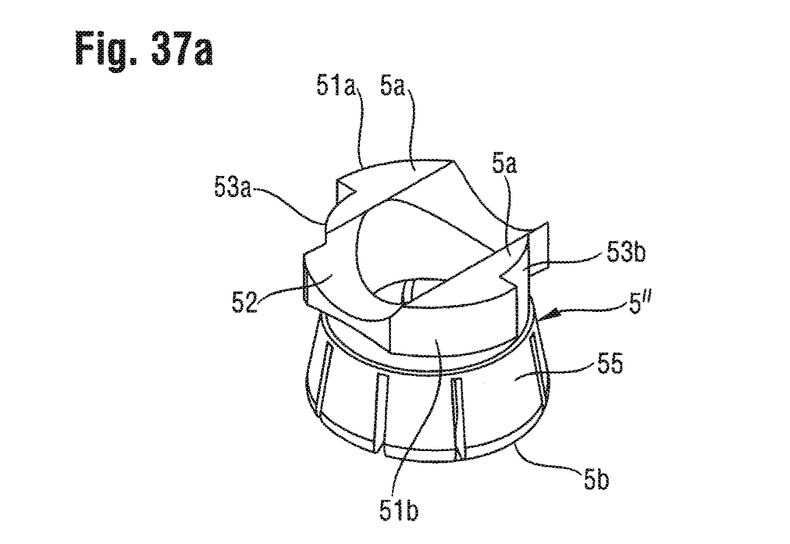
FIGS. 37a and 37b show perspective views of a head receiving part of a polyaxial bone anchoring device according to a further alternate embodiment.
Figure 37B:
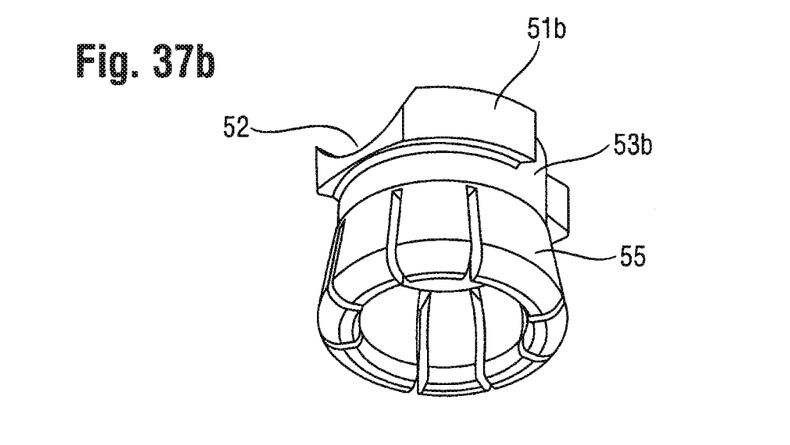

In FIGS. 37a and 37b, a head receiving part of a further alternate embodiment is shown. In FIGS. 37a and 37b, a head receiving part 5" is shown with a configuration different from the head receiving part from the first embodiment. Namely, the rim portions 51a and 51b have a different configuration, which can be described as being on opposite portions of the head receiving part 5", as compared to the rim portions of the head receiving part of the first embodiment.

Figure 38A:
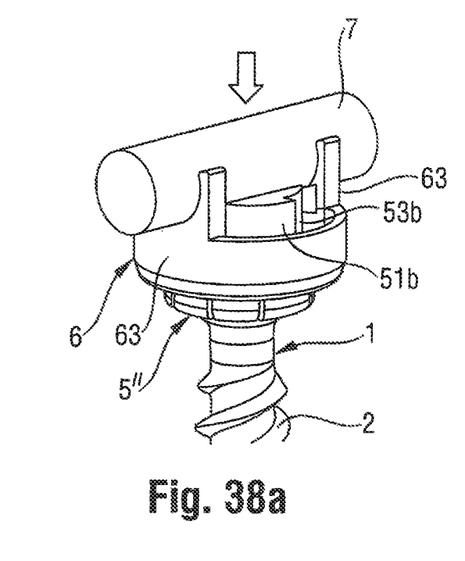
FIGS. 38a to 38c show steps of assembly and use of the polyaxial bone anchoring device according to the further alternate embodiment.
Figure 38B:
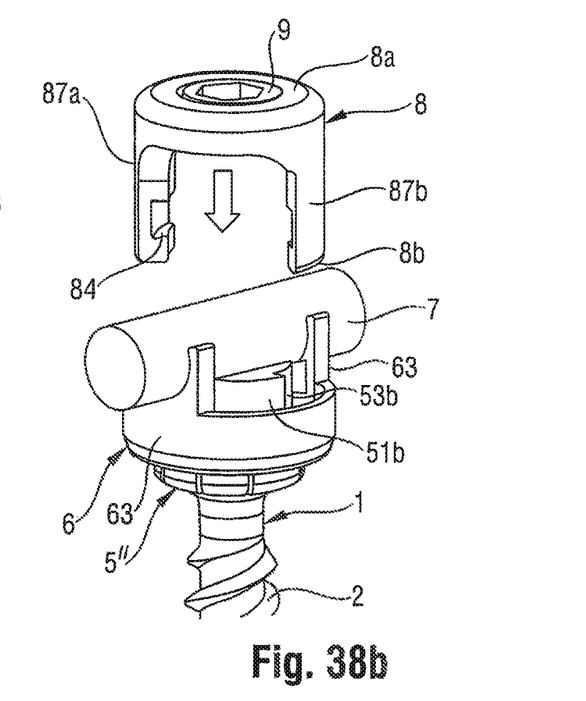
Figure 38C:
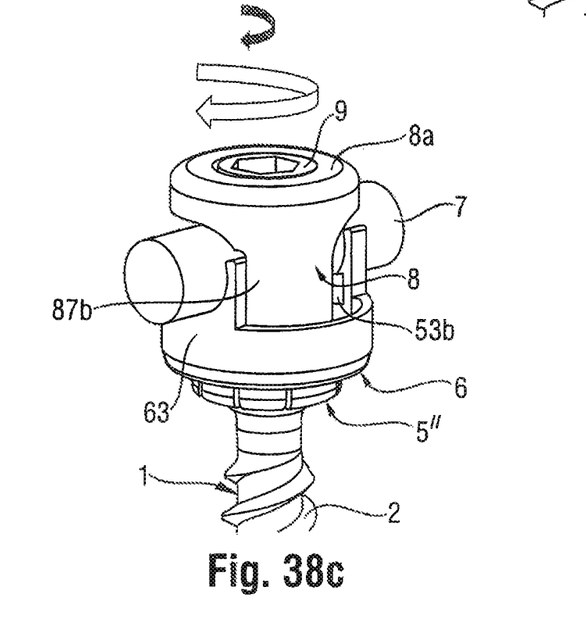

In FIGS. 38a to 38c, a further alternate embodiment of a polyaxial bone anchoring device includes the head receiving part 5" shown in FIGS. 37a and 37b. The assembly of the bone anchoring device in FIGS. 38a to 38c is similar to that shown in FIGS. 20 to 22, with the exception that in FIGS. 38a to 38c, the cap 8 and the locking element 9 are tightened in the same direction, whereas in FIGS. 20 to 22, the cap 8 and the locking element 9 are tightened in opposite directions. The alternate steps illustrated in FIGS. 38a to 38c may follow the step shown in FIG. 19.

In FIG. 38a, the rod 7 is inserted into the recesses 64 provided at the projections 63. Because the recesses 64 have circular segment shapes including a largest diameter of the rod 7, the rod 7 can be caught or held in the recesses 64, so that it is preliminarily held in place therein.

In a next step, as shown in FIG. 38b, the cap 8 is placed onto the rest of the assembly. The locking element 9 may be pre-assembled with the cap 8. In the first position, the legs 87a, 87b extend along or are aligned with the cutouts 53a, 53b, and thus extend into spaces between the projections 63 of the locking ring 6 and the rim portions 51a, 51b of the head receiving part 5".

Next, as shown in FIG. 38c, the cap 8 is rotated so that undercut portions 84 engage undercut portions 51c at the rim portions 51a, 51b of the head receiving part 5". In this second position, the cap 8 is prevented from being pulled away from the rest of the assembly in an axial direction. Then, the locking element 9 is tightened in the same direction as the cap 8. For example, both locking element 9 and cap 8 may be rotated clockwise, or alternatively, both may be rotated counterclockwise, in order to be tightened or locked. The tightening of both the locking cap 8 and the locking element 9 in a same direction is enabled by the alternate arrangement of the cutouts 53a, 53b and the rim portions 51a, 51b. Namely, the cutouts 53a, 53b are oriented to be upstream of the rim portions 51a, 51b, with respect to the direction of locking of both the cap 8 and the locking element 9. Because the cap 8 and the locking element 9 are tightened in the same rotational direction, the locking force of locking the assembly is increased. In addition, with a same direction of locking, tightening of the locking element 9 will not result in inadvertent loosening of cap 8.

Upon tightening, the lower surface of locking element 9 contacts the rod 7 and the rod 7 is pressed into the recesses 64 of the projections 63 of the locking ring 6. The force acting onto the rod 7 is transferred to the locking ring 6, and the locking ring 6 is shifted downwards to firmly compress the head receiving part 5" and lock the head 3 therein. The head 3 and the rod 7 may be locked simultaneously upon fixing or locking the assembly. When tightening the locking element 9, the connection between the head receiving part 5" and the cap 8 may also be reinforced.

It shall be understood that various modifications of the embodiments shown are also possible. Any engagement structure of the cap and the head receiving part that prevents pulling off of the cap when in an engaged position can be implemented. In particular, a size of rim portions or of dovetail grooves in a circumferential direction may be different from the embodiments shown.

Other modifications are also conceivable. For example, the configurations of the locking ring and of the cooperating outer surface portion of the head receiving part can be designed in other ways. For example, an the inner surface of the locking ring can be tapered and cooperate with a tapered outer surface of the head receiving part. In a further example, an outer surface portion of the head receiving part can be convexly rounded, and an inner surface of the locking ring can be straight or tapered. In some embodiments, the cooperating surfaces of the locking ring and the head receiving part can also be parallel, so that the clamping of the head is achieved by an interference fit between the locking ring and the head receiving part.

For the bone anchoring element, various bone anchoring elements can be used that differ with respect to their shank lengths, diameters, or thread foul's. Some bone anchoring elements may have a through channel with openings for introducing of drugs or bone cement. Also, hooks, nails, or any other anchoring elements can also be used.

The various rod receiving recesses can also be semi-circular, quarter-circular, or U-shaped, or can have various other shapes that are configured to accommodate a rod therein.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A poly-axial bone anchoring device comprising:
a bone anchoring element having a shank for anchoring to a bone and a head;
a head receiving part having a first end, an open second end, and a hollow interior portion in communication with the open second end for receiving the head therein, the head receiving part being flexible for clamping the head;
a locking ring configured to be mounted around the head receiving part, the locking ring comprising a rod receiving portion;
a cap configured to be connected to the head receiving part, the cap having a first end, a second end, a central axis extending through the first and second ends of the cap, and two opposite legs extending in a direction of the central axis; and
a locking element configured to extend from the cap to engage an inserted rod and to lock relative positions of the bone anchoring element and inserted rod relative to the head receiving part;
wherein when the head is in the head receiving part and the locking ring is around the head receiving part, the head is pivotable in the head receiving part and can be locked at an angle relative to the head receiving part by compressing the head receiving part with the locking ring; and
wherein the cap is rotatable relative to the head receiving part between a first position in which the cap is movable axially in a first direction away from the second end of the head receiving part and a second position in which the legs engage the head receiving part to prevent movement of the cap in the first direction and to hold an inserted rod between the cap and the head receiving part.

2. The bone anchoring device of claim 1, wherein the head receiving part further comprises a portion adjacent to the first end with an undercut for engagement by the cap.

3. The bone anchoring device of claim 1, wherein the head receiving part further comprises two diametrically opposed radial projections for engagement with the cap.

4. The bone anchoring device of claim 3, wherein the head receiving part has a portion arranged along a longitudinal axis for receiving an inserted rod, and wherein the radial projections are arranged substantially at 30° to 60° relative to the longitudinal axis.

5. The bone anchoring device of claim 4, wherein a space is defined between the radial projections and the portion of the head receiving part for receiving an inserted rod, and wherein a width of the legs in a circumferential direction is less than or equal to the space.

6. The bone anchoring device of claim 1, wherein a flexible region of the head receiving part has an outer surface with an outer diameter that increases towards the open second end.

7. The bone anchoring device of claim 1, wherein a flexible region of the head receiving part comprises a wall having a plurality of slits.

8. The bone anchoring device of claim 1, wherein the head has a spherical outer surface portion, and wherein the hollow interior portion of the head receiving part defines a spherical seat portion for the head.

9. The bone anchoring device of claim 1, wherein the head receiving part has a through hole at the first end in communication with the hollow interior portion, the through hole having a diameter smaller than a greatest diameter of the head.

10. The bone anchoring device of claim 1, wherein the rod receiving portion of the locking ring comprises two projections diametrically opposite to each other, the projections each having a recess for receiving and preliminarily holding a rod therein.

11. The bone anchoring device of claim 10, wherein the recess of each projection has a contour forming a circular segment defining more than a semicircle.

12. The bone anchoring device of claim 1, wherein the cap is substantially cylindrical and has two diametrically opposite recesses open to the second end of the cap for a rod to pass through.

13. The bone anchoring device of claim 1, wherein the cap has a threaded through hole, and wherein the locking element is a set screw configured to be arranged in the through hole.

14. The bone anchoring device of claim 1, wherein the cap has an undercut portion for the engagement with the head receiving part.

15. The bone anchoring device of claim 1, wherein the head receiving part has a dovetail groove and the legs of the cap each has a dovetail portion for engagement with the dovetail groove.

16. The bone anchoring device of claim 1, wherein the head receiving part has a rod guiding recess at the first end.

17. The bone anchoring device of claim 1, wherein a direction of rotation of the cap from the first position to the second position relative to the head receiving part is the same as a direction of rotation for advancing the locking element relative to the cap to lock the bone anchoring device.

* * * * *

UNITED STATES PATENT AND TRADEMARK OFFICE
CERTIFICATE OF CORRECTION

| | | |
|---|---|---|
| PATENT NO. | : 9,017,390 B2 | Page 1 of 1 |
| APPLICATION NO. | : 13/673837 | |
| DATED | : April 28, 2015 | |
| INVENTOR(S) | : Lutz Biedermann et al. | |

It is certified that error appears in the above-identified patent and that said Letters Patent is hereby corrected as shown below:

In the Specification

Column 4, line 53     Delete "it"
                      Insert -- fit --

Column 5, line 25     Delete "an,"
                      Insert -- an --

Column 8, line 65     Delete "foul's"
                      Insert -- forms --

In the Claims

Column 9, Claim 1, line 14     Delete "poly-axial"
                               Insert -- polyaxial --

Column 10, Claim 15, line 44   Delete "has"
                               Insert -- have --

Signed and Sealed this
Twenty-third Day of February, 2016

Michelle K. Lee
*Director of the United States Patent and Trademark Office*